United States Patent [19]

Melcher et al.

[11] Patent Number: 4,999,105

[45] Date of Patent: Mar. 12, 1991

[54] APPARATUS FOR MEMBRANE ASSISTED LIQUID CHROMATOGRAPHY

[75] Inventors: Richard G. Melcher; Hernan J. Cortes, both of Midland, Mich.

[73] Assignee: The Dow Chemical Company, Midland, Mich.

[21] Appl. No.: 229,182

[22] Filed: Aug. 5, 1988

Related U.S. Application Data

[63] Continuation of Ser. No. 115,795, Nov. 2, 1987, Pat. No. 4,775,476.

[51] Int. Cl.$^5$ .............................................. B01D 15/08
[52] U.S. Cl. ................................. 210/198.2; 210/259; 210/321.78
[58] Field of Search ............... 210/659, 198.2, 198.3, 210/656, 635, 259, 321.78, 637; 55/386; 73/61.1 C; 422/70; 436/161

[56] References Cited

U.S. PATENT DOCUMENTS

| | | | |
|---|---|---|---|
| 3,686,117 | 8/1972 | Lauer | 210/659 |
| 4,070,284 | 1/1978 | Fujita | 210/659 |
| 4,112,743 | 9/1978 | Mowery | 210/659 |
| 4,271,697 | 6/1981 | Mowery | 210/659 |
| 4,446,105 | 5/1984 | Dinsmore | 210/659 |
| 4,500,430 | 2/1985 | Dasguta | 210/656 |
| 4,529,521 | 7/1985 | Cortes | 210/635 |
| 4,544,485 | 10/1985 | Pinkerton | 210/656 |
| 4,676,897 | 1/1987 | Kuze | 210/659 |
| 4,699,718 | 10/1987 | Jones | 210/659 |
| 4,715,217 | 12/1987 | Coyne | 73/61.1 C |
| 4,913,821 | 4/1990 | Melcher | 210/659 |

OTHER PUBLICATIONS

Snyder, Introduction to Modern Liquid Chromatography, John Wiley & Sons, Inc. 1979, pp. 113–117.
Mikes Laboratory Handbook of Chromatographic and Allied Methods, Ellis Horwood Limited, Chichester, pp. 440–441, 540, 541.

*Primary Examiner*—Ernest G. Therkorn
*Attorney, Agent, or Firm*—Timothy S. Stevens

[57] ABSTRACT

Apparatus and method for extracting a component from a sample across a membrane into an extractant and then injecting the extracted sample component into a chromatographic eluent and onto a chromatographic column to chromatographically analyze the extracted sample component. In essence, the advance provided by this invention is that the extractant and the eluent are the same and only one pump is used for pumping the eluent and extractant. In prior apparatus and methods in this field, the extractant and the eluent were separate and each had its own pump.

8 Claims, 3 Drawing Sheets

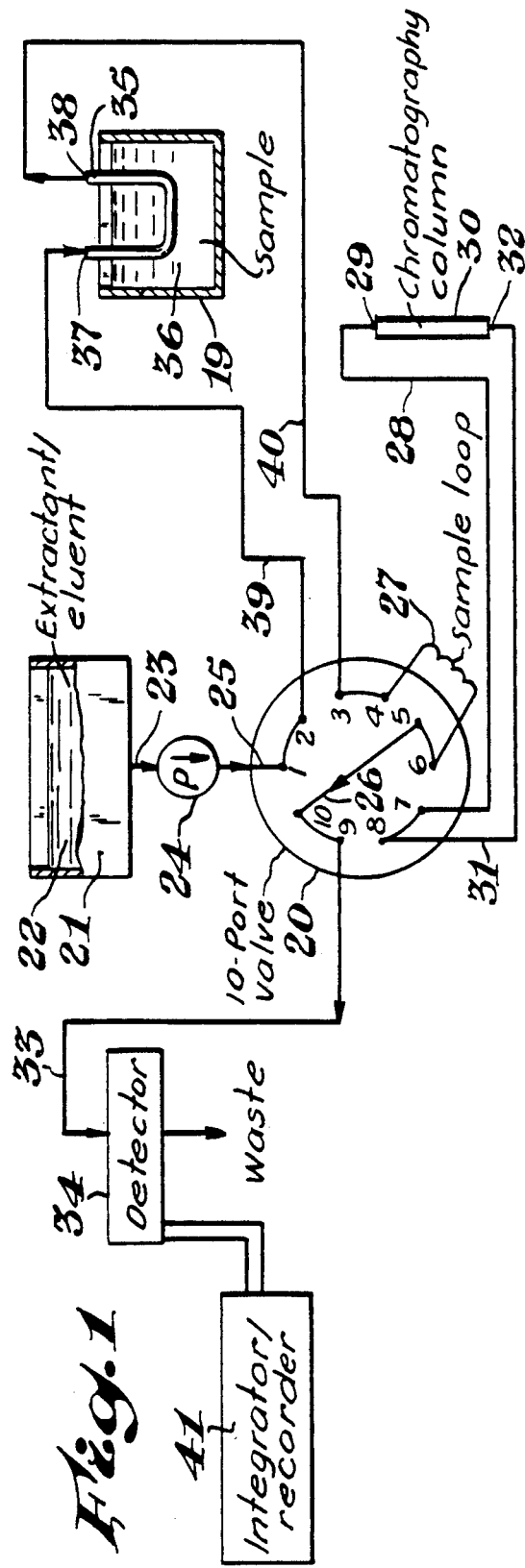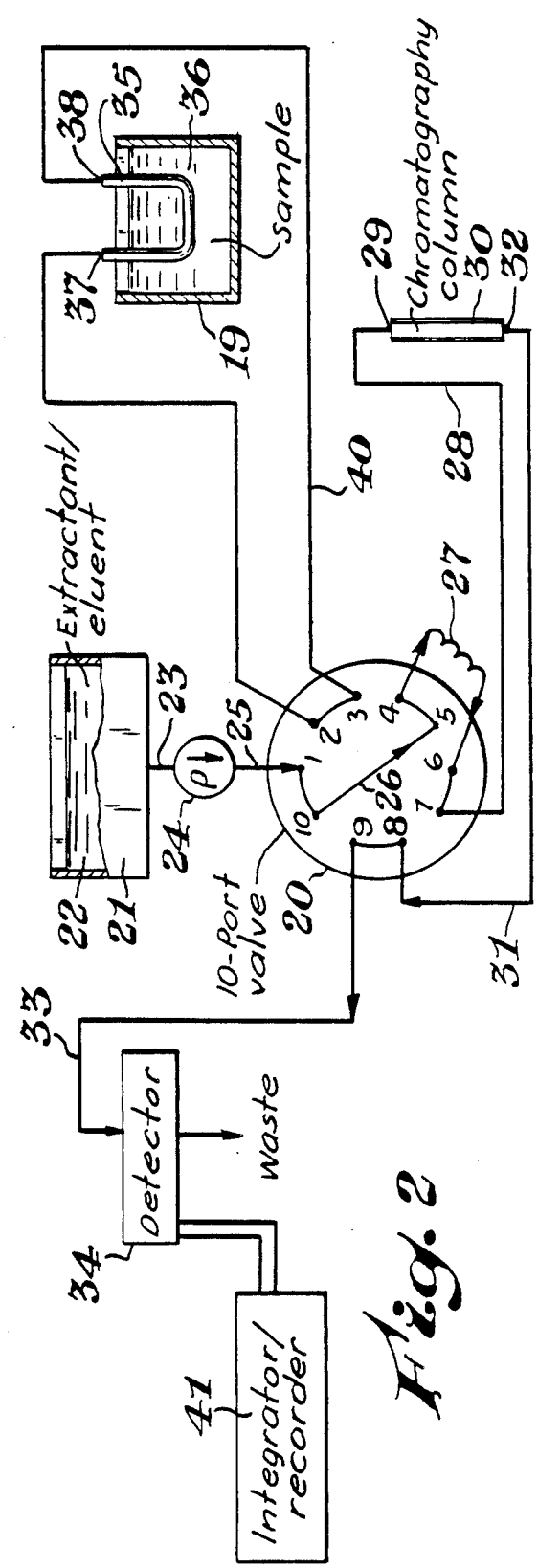

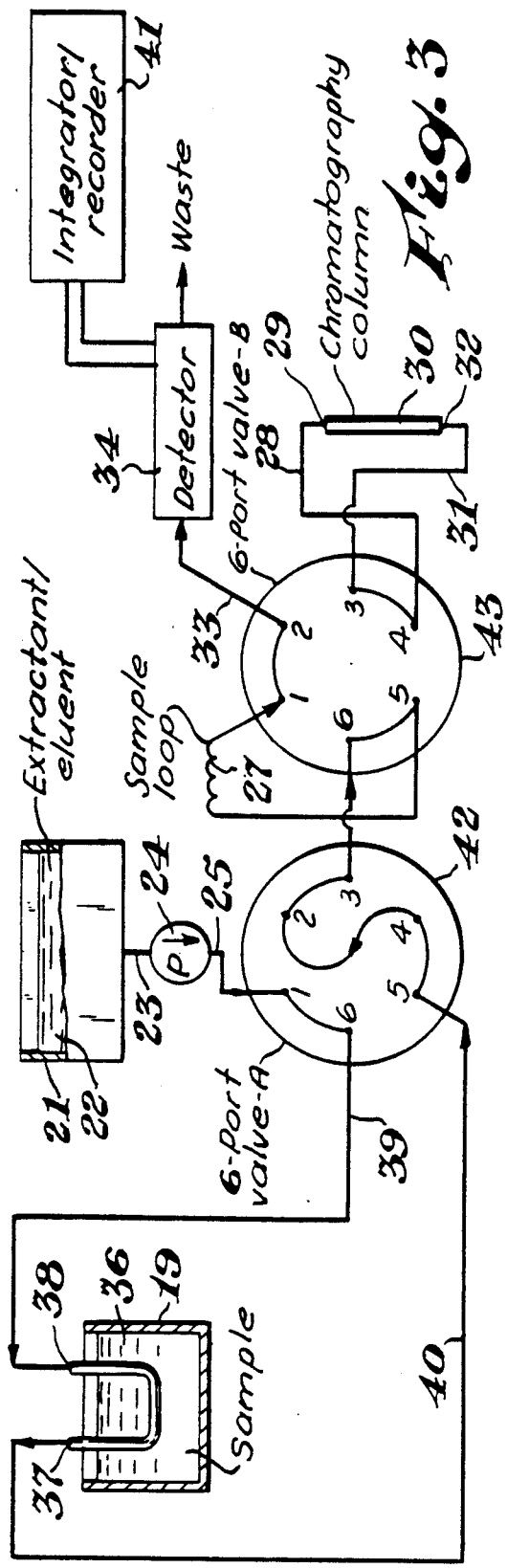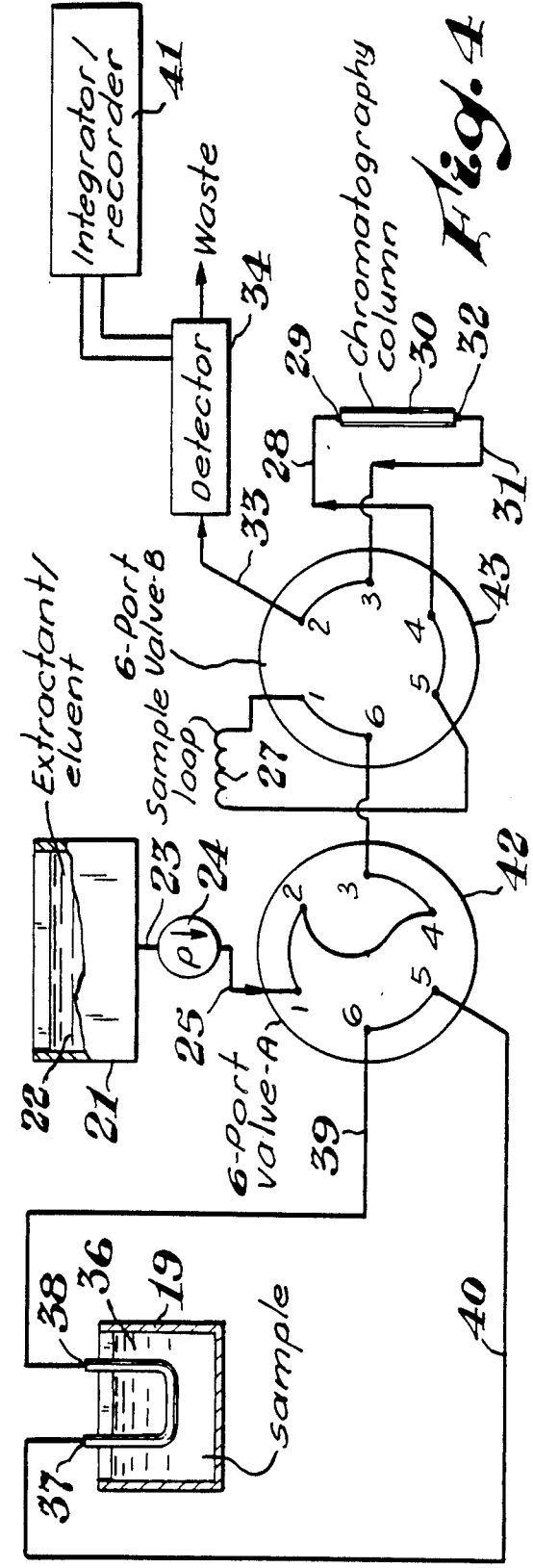

APPARATUS FOR MEMBRANE ASSISTED LIQUID CHROMATOGRAPHY

CROSS REFERENCE TO RELATED APPLICATION

This is a continuation of application Ser. No. 115,795, filed Nov. 2, 1987, now U.S. Pat. No. 4,775,476.

FIELD OF THE INVENTION

The invention is in the field of liquid chromatography and more specifically in the field of using membranes to pretreat samples to be analyzed by liquid chromatography.

BACKGROUND OF THE INVENTION

The chemical analysis technique comprising partitioning a sample containing a sample component of interest from a liquid extractant with a membrane is known. The sample component of interest permeates through the membrane into the extractant which can then be analyzed to determine the component of interest. The specific membrane and extractant used are selected to enhance the extraction of the sample component of interest and to minimize or eliminate the extraction of other components of the sample that may not be of interest or that may interfere with the determination of the component of interest. One means used to determine a sample component of interest in the extractant is liquid chromatography and the overall system is then termed "membrane assisted liquid chromatography". In membrane assisted liquid chromatography a preselected volume of extractant containing the extracted sample component of interest is injected into a liquid chromatographic system and the sample component of interest is thereby determined.

One example of membrane assisted liquid chromatography is described in U.S. Pat. No. 4,529,521 to Hernan J. Cortes and James C. Davis. A sample of synthetic latex solution is partitioned from a water extractant by a bundle of dialysis type hollow fiber membranes. The water extractant is positioned in the bores of the hollow fibers and relatively low molecular weight components in the latex solution permeate through the membrane into the extractant. A syringe filled with water is used to pump the extractant from the bores of the hollow fibers into the injection loop of a liquid chromatography injection valve in the load position. A liquid chromatography pump is used to pump dilute sulfuric acid eluent through the injection valve, through a liquid chromatography column and then to a liquid chromatography photometric detector. When the injection valve is placed in the inject position, the eluent pumps the extractant in the injection loop onto the column and the extracted relatively low molecular weight components of the latex solution are chromatographed and eventually emerge from the column to be detected by the detector. If the latex sample is injected directly onto the column, the latex particles will soon plug the column.

The use of a membrane to pretreat a sample that can not be directly injected is a significant improvement in the art of liquid chromatography. However, at least one problem remains with this approach at its present state of development. This problem is the complexity of known membrane assisted liquid chromatography systems in that two solutions are used (extractant and eluent) and two pumping means are needed, one for the extractant and one for the eluent. The present invention is a solution to this problem.

SUMMARY OF THE INVENTION

In the method of the present invention, the same solution is used as both the extractant and the eluent. In the apparatus of the present invention, a single pumping means is used for pumping the eluent and extractant.

The apparatus of the present invention comprises six elements. The first element is a means for pumping a liquid such as a liquid chromatography eluent pump. The second element is a membrane having a first side and a second side such as a tubular shaped membrane. The third element is a channel having a first end and a second end, at least a portion of the channel being formed by the first side of the membrane so that the second side of the membrane can be exposed to a sample containing a sample component. The fourth element is an injection conduit having a first end and a second end for containing a preselected volume of the the liquid such as an injection loop, e.g., a preselected length of tubing. The fifth element is a liquid chromatography column for chromatographing the sample component, the liquid chromatography column having an inlet port. The sixth element is a means for switching liquid flow between a first flow pattern and a second flow pattern, being in liquid communication with: the means for pumping the liquid: the first end of the channel; the second end of the channel; the first end of the injection conduit; the second end of the injection conduit; and the inlet port of the chromatography column. The first flow pattern being from the pumping means through the channel and through the injection conduit. The second flow pattern being from the pumping means, through the injection conduit, to the inlet port of the liquid chromatography column. The means for switching liquid flow between a first flow pattern and a second flow pattern can be one or more multi-port valves such as a 10-port valve, an 8-port valve or a pair of 6-port valves.

The method of the present invention comprises five steps. The first step is to flow a liquid extractant/eluent into contact with one side of a two sided membrane, e.g., flowing the extractant/eluent into the bore of a tubular membrane. The second step is to contact the other side of the membrane with a sample so that a component of the sample permeates through the membrane into the extractant/eluent to form a dispersion of the sample component in the extractant/eluent. The third step is to flow the dispersion of the sample component in the extractant/eluent into an injection conduit, e.g., flowing the dispersion of the sample component in the extractant/eluent into an injection loop. The fourth step is to flow the extractant/eluent into the injection conduit so that the dispersion of the sample component in the extractant/eluent in the injection conduit is flowed into a chromatographic column which chromatographs the sample component so that at least a portion of the sample component eventually emerges from the chromatographic column dispersed in the extractant/eluent emerging from the chromatographic column. The fifth step is to detect the sample component dispersed in the extractant/eluent emerging from the chromatographic column, e.g., to detect the sample component dispersed in the extractant/eluent emerging from the chromatographic column using a photometric liquid chromatography detector or an electrochemical liquid chromatography detector.

BRIEF DESCRIPTION OF THE DRAWINGS

FIG. 1 is a schematic drawing of an apparatus embodiment of the invention including a two position 10-port valve in one position;

FIG. 2 is a schematic drawing of the embodiment of FIG. 1 with the two position 10-port valve in the other position;

FIG. 3 is a schematic drawing of an apparatus embodiment of the invention including a pair of two position 6-port valves in one position;

FIG. 4 is a schematic drawing of the embodiment of FIG. 3 with the pair of two position 6-port valves in the other position;

DETAILED DESCRIPTION OF THE INVENTION

Figure 5:
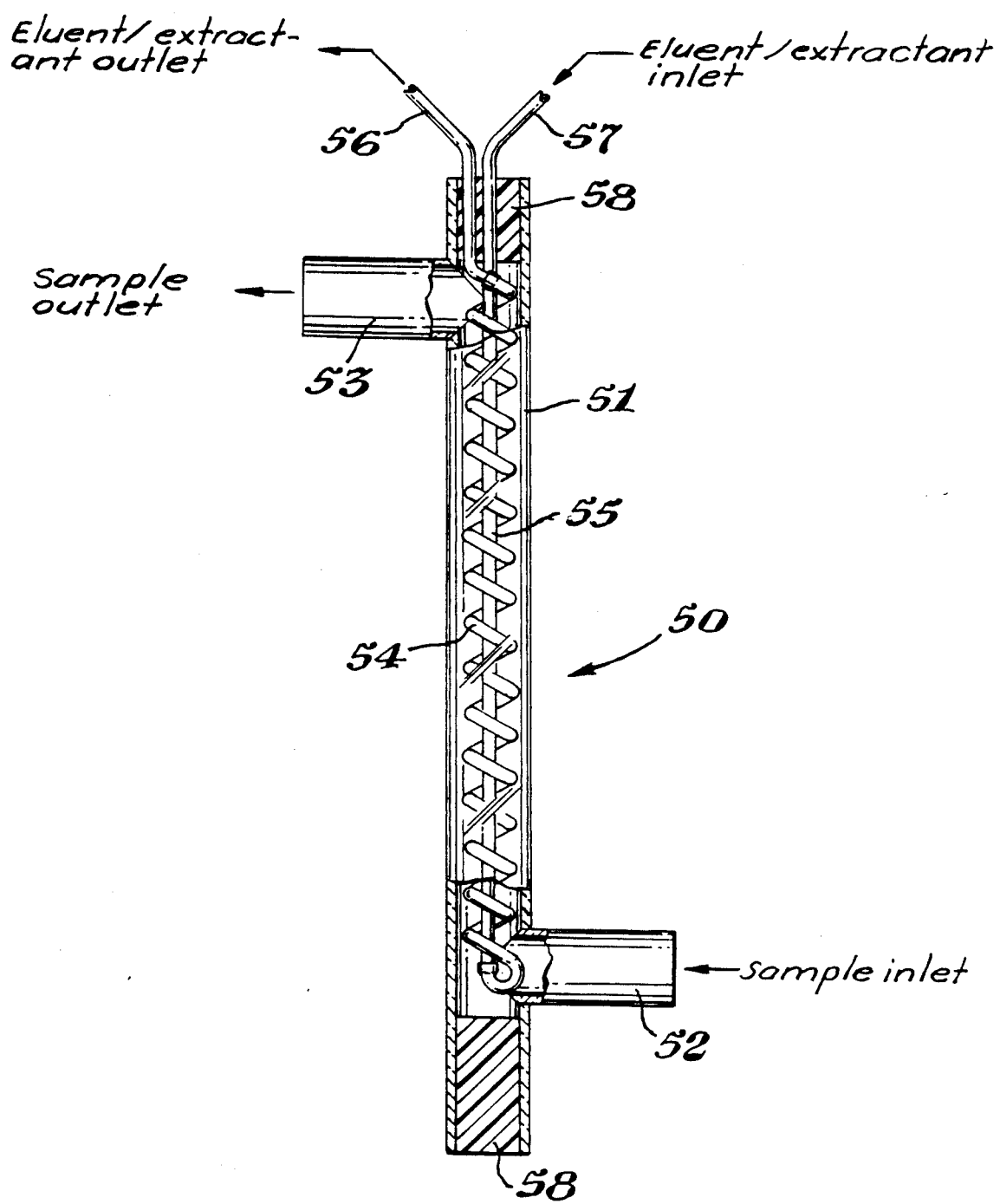
FIG. 5 is a front view of a preferred membrane cell for use in the invention.

Referring to FIGS. 1 and 2, therein is shown a schematic drawing of an apparatus embodiment of the invention including a two position 10-port valve 20 (such a valve is available from the Anspec Co., Ann Arbor, Mich., as the Valco 10-Dort multi-function sampling valve, Catalog no. H1765) shown in one position in FIG. 1 and in the other position in FIG. 2. The valve 20 is a preferred means for switching liquid flow between a first flow pattern and a second flow pattern. The specific means used for this switching is not critical to the invention and many different multi-port valve constructions can be used as will be discussed in further detail below in reference to FIGS. 3 and 4. A reservoir 21 is provided for containing a liquid extractant/eluent 22. A length of tubing 23 connects the reservoir 21 with a liquid chromatography pump 24 (available from Anspec, supra, as the ConstaMetric IIIG pump, as Catalog No. F1025). The specific pumping means used is not critical to the invention as long as it is suitable for the liquid chromatography of the invention. The pump 24 is connected (1/16 stainless steel tubing and fittings used generally throughout herein for such connections and is available from Anspec, supra) to port 1 of the valve 20 by a length of tubing 25. The valve 20 internally connects the valve ports as shown, i.e., ports 1-2, 3-4, 5-6, 7-8, 9-10 in FIG. 1, and ports 2-3, 4-5, 6-7, 8-9, 10-1 in FIG. 2. A length of tubing 26 is used to connect port 10 to port 5. A sample loop 27 is connected to port 4 and port 6 of the valve 20. The sample loop 27 is a preferred example of a conduit having a preselected volume for injecting a liquid contained in the preselected volume into a flowing stream of liquid and this conduit can take other forms such as a conduit that is internally machined into a valve. A length of tubing 28 is used to connect port 7 of the valve 20 and an inlet port 29 of a liquid chromatography column 30. Another length of tubing 31 is used to connect port 8 of the valve 20 and an outlet port 32 of the column 30. The specific column 30 used is not critical to the invention and can include capillary columns, packed capillary columns, packed microbore columns, packed columns, semi-prep columns and prep columns. A 4-port valve, not shown, (for example, Anspec Catalog No. A7752) can be installed between the column 30 and the 10-port valve 20 to reverse flow through the column 30, if desired. A length of tubing 33 is used to connect port 9 of the valve 20 to a liquid chromatography detector 34. The specific detector 34 used is not critical to the invention and can include photometric detectors and electrochemical detectors.

FIGS. 1 and 2 also schematically show a tubular membrane 35 immersed in a sample 36 which is contained in a cup 19. The bore of the tubular membrane 35 defines a channel having a first end 37 and a second end 38. The outside of the membrane 35 is exposed to the sample 36. A length of tubing 39 connects port 2 of the valve 20 to the first end 37 of the channel and another length of tubing 40 connects port 3 of the valve 20 to the second end 38 of the channel.

Referring to FIG. 1, a specific flow pattern is shown and critically includes a flow pattern of from the pump 24, through the valve 20, through the bore of the membrane 35, and then into the sample loop 27. This flow pattern allows the extractant/eluent 22 to be flowed into contact with the inside of the membrane 38. The outside of the membrane 38 is contacted with the sample 36 so that generally more than one component of the sample (and critically at least one component of the sample) can permeate through the membrane into the extractant/eluent in the bore of the membrane 38 to form a dispersion of the sample components in the extractant/eluent in the bore of the membrane 38. Continuing flow of the extractant/eluent 22 in the tubing 39 flows the dispersion of the sample components in the extractant/eluent in the bore of the membrane 35 into the tubing 40 and then into the sample loop 27. Since the components of the sample generally continuously permeate through the membrane 38, it is often preferable to continue pumping the extractant/eluent 22 into the bore of the membrane 38 so that the dispersion of the sample components in the extractant/eluent continues to flow into and then through the sample loop 27, through the tubing 26 and 33 to the detector 34. In this event, it is often possible to monitor the sample components in the extractant/eluent with the detector 34 to insure that a generally preferable steady state of permeation of the sample components has been achieved before switching valve 20 to the position shown in FIG. 2.

Referring to FIG. 2, a specific flow pattern is shown and critically includes a flow pattern of from the pump 24, through the valve 20, through the sample loop 27, through the column 30, through the valve 20 and then to the detector 34. This flow pattern allows the extractant/eluent to flow into the sample loop 27 so that the dispersion of the sample components in the extractant-/eluent in the sample loop 27 is flowed into the column 30 for chromatographic retention of at least one sample component and preferably a chromatographic separation of all of the sample components so that at least a portion of one of the sample components eventually emerges from the column 30 in the extractant/eluent emerging from the chromatographic column 30 (from the port 32) and then flows through the valve 20 to the detector 34. The detector 34 detects at least one sample component and generally outputs to an integrator recorder 41 as is well known in the art.

When the valve 20 is in the position shown in FIG. 2, there is essentially no flow of extractant/eluent in the bore of the membrane 35 and a relatively high concentration of the permeated sample components can build up in the extractant/eluent in the bore of the membrane 35 over an extended period of time, e.g. 10 minutes. If desired, this characteristic can be beneficially used to increase detection sensitivity of the permeated sample components by switching the valve 20 to the position shown in FIG. 1 only long enough to move the relatively high concentration of the permeated sample components into the sample loop 27 and then switch the valve 20 back to the position shown in FIG. 2 for a chromatographic separation of the components.

Referring to FIG. 1, the column 30 is isolated from the flow pattern so that the membrane 38 will not be subjected to the relatively high pressures often generated when pumping a liquid eluent through a liquid chromatography column. Referring to FIG. 2, the membrane 38 is isolated from the flow pattern so that, as in above, the membrane 38 will not be subjected to the relatively high pressures often generated when pumping a liquid eluent through a liquid chromatography column. The embodiment of the invention shown in FIGS. 1 and 2 demonstrates one of the principal advantages of the present invention in that the extractant is the same as the eluent and only one pump is used. The invention requires that the extractant perform satisfactorily as an eluent and vice versa but the extensive knowledge available to the liquid chromatographer about the many different eluent compositions used in liquid chromatography (including reverse phase, normal phase, ion exchange, size exclusion, and hydrodynamic chromatography) should be an advantage when one skilled in the art of liquid chromatography uses the present invention.

Referring to FIGS. 3 and 4, therein is shown a schematic drawing of another apparatus embodiment of the invention including a pair (A and B) of two position 6-port valves 42 and 43 (such as valves available from Anspec, supra, as a pair of Rheodyne Type 70 switching valves, Catalog No. F1131, preferably mounted on a Catalog No. H1687 tandem solenoid actuator so that each valve can be switched at essentially the same time). An understanding of this embodiment is readily apparent from the above discussion of FIGS. 1 and 2 except that the valve port numbers may be different. It should be understood that many specific valve systems incorporating one or more valves could be used in the invention as the means for switching between two flow patterns. For example, the valve 42 in FIGS. 3 and 4 could be a 4-port valve and the valve 20 in FIGS. 1 and 2 could be an 8-port valve. It is believed that the 10-port valve 20 is the best since it is commercially available and involves only one valve body. An air actuated 8-port valve suitable for use in the invention is available from the Valco Co., Houston, Tex., as part number AC8W. In any event, a critical feature of the means for switching the extractant/eluent flow between a first flow pattern and a second flow pattern is that the means be in liquid communication, e.g., by 1/16 inch diameter stainless steel tubing, with the means for pumping the extractant/eluent, with each end of the membrane 35, with each end of the sample loop 27 and with the inlet port 29 of the column 30.

The specific type of membrane used is not critical to the invention. The membrane can be flat in shape and form a portion of a channel cut, for example, in a stainless steel or Teflon ® block. The membrane can be tubular in shape and the tube can be relatively small in diameter, e.g., 0.025 inches or smaller, or relatively large in diameter, e.g., 0.1 inches or larger. The membrane can be of the porous type or the non-porous type. The membrane can be hydrophilic or hydrophobic. Critically, the membrane should not rapidly deteriorate, e.g., dissolve, in the extractant/eluent or the sample. Critically, the membrane should permeate at least one component of the sample to the extractant/eluent when the membrane partitions the two. A preferred membrane is a tubular silicone rubber membrane.

EXAMPLE 1

The system shown in FIGS. 1 and 2 (except that a different membrane configuration is used as described below) is assembled and includes a Hewlett Packard Hypersil ODS 5 micron liquid chromatography column 30 (2.1 mm × 100 mm), a Kratos Spectroflow 773 variable wavelength liquid chromatography detector 34 (set at 254 nanometers) and a Spectraphysics 4270 integrator-recorder 41. The eluent/extractant 22 is 50% acetonitrile, 50% water, 0.02M in phosphoric acid pumped at a flow rate of 200 microliters per minute. The sample loop 27 contains a fixed volume of 100 microliters.

A membrane cell 50, preferred for polar eluent/extractants, is assembled as shown in FIG. 5. A 150 mm long 2 mm internal diameter glass tube 51 is provided with a sample inlet neck 52 and a sample outlet neck 53. The membrane 54 used is Dow Corning Silastic ® Medical Tubing (0.012 inches internal diameter, 0.025 inches external diameter, 100 mm long) and is spiral wound on a 60 mm long length of 1/32 inch outside diameter Teflon ® tubing 55. One end of the tubing 55 is the eluent/extractant inlet 57. The other end of the tubing 55 is joined to one end of the membrane 54 by first swelling the end of the membrane 54 in xylene, inserting the end of the tubing 55 into the end of the swollen membrane 54 and then allowing the xylene to evaporate to shrink the membrane 54 onto the tubing 55 so that a leak tight joint is formed. The other end of the membrane 54 is similarly joined to an eluent/extractant outlet 56 which is also made from 1/32 inch diameter Teflon ® tubing. The ends of the tube 51 are each sealed with Dow Corning ® RTV Silicone Rubber Sealant 58. The membrane cell 50 is highly preferred for polar eluent/extractants, e.g. water based eluent/extractants, because it is easily made and provides excellent contact between the sample and the membrane 54 when the sample is flowed into the sample inlet neck 52. In non-polar eluent/extractants, e.g., toluene, the membrane 54 can swell excessively and cause blocked flows. In this event a cell is preferred wherein the silicone rubber membrane is assembled in a stretched condition so that when it swells the degree of stretch is substantially reduced or a cell where the length of membrane can be subsequently adjusted to accommodate the swollen membrane. Alternatively, a cell can be assembled with the membrane already in the swollen condition.

A sample containing 1 ppm (parts per million) each of the sample components benzene, toluene, styrene and ethyl benzene in water is flowed into the sample neck 52 at a flow rate of about 1 ml per minute with the system flow pattern as shown in FIG. 1. The integrator/recorder 41 initially shows that the absorbance of the extractant/eluent flowing through the detector 34 is not increased. However, the absorbance of the extractant/eluent flowing through the detector 34 soon increases and then reaches a steady state. The valve 20 is then rotated to the position shown in FIG. 2 and the integrator/recorder 41 then traces a chromatogram over the next 10 minutes showing a separate peak for benzene, toluene, styrene and ethyl benzene each of a given peak area and peak height.

This example teaches how to make a preferred membrane cell for use in the invention and how to determine sample components with the invention.

EXAMPLE 2

The system of Example 1 is used in this example and the experiment of Example 1 is continued. The valve 20 is left in the position shown in FIG. 2 for 11 minutes (during which time the eluent/extractant in the bore of the membrane 54 is not flowing which generally increases the concentration of the permeated sample components therein) and then is switched to the position shown in FIG. 1 for a time needed to transport the permeated sample components from the bore of the membrane 54 into the sample loop 27. Then the valve 20 is rotated back to the position shown in FIG. 2 and the integrator/recorder 41 then traces a chromatogram over the next 10 minutes showing a separate peak for benzene, toluene, styrene and ethyl benzene each of a peak height and peak area greater than in Example 1. The peak height and area of the benzene peak is about 3.5 times greater. The peak height and area of the toluene peak is about 4.2 times greater. The peak height and area of the styrene peak is about 4.5 times greater. The peak height and area of the ethyl benzene peak is about 6.3 times greater.

In this example the sample is fed into the sample inlet port 52 of the membrane cell 50 of FIG. 5. Alternatively, water could have been fed into the sample inlet port 52 of the membrane cell 50 of FIG. 5 and the sample could have been injected into the water and carried by it into contact with the membrane 54. In this event, the detector sees a "peak" resulting from injection of a sample if the valve 20 is not rotated when the permeated sample component(s) flow through the sample loop 27 and this mode of analysis can be used if a chromatographic separation of the permeated sample component(s) is not desired.

This example teaches how to gain better sensitivity of analysis with the invention.

EXAMPLE 3

The system of Example 2 is changed so that the Column 30 is a Brownlee 10 micron PRP-1 (4.6 mm × 30 mm), the eluent/extractant 22 is 0.01N NaOH containing 2.5% acetonitrile, and the detector 34 is changed to an LDC/Milton Roy e c Monitor electrochemical detector set at +0.55 volts, and the sample is changed to a sample containing 100 ppb (parts per billion) of the sample component phenol and 20 ppb of the sample component 2-chlorophenol, in water. The valve 20 is placed in the position shown in FIG. 1 until steady state permeation is indicated and then the valve 20 is placed in the position shown in FIG. 2 for 15 minutes. Then the valve 20 is switched to the position shown in FIG. 1 for a time needed to transport the permeated sample components from the bore of the membrane 54 into the sample loop 27. Then the valve 20 is rotated back to the position shown in FIG. 2 and the integrator/recorder 41 then traces a chromatogram over the next 10 minutes showing a separate peak for phenol and 2-chlorophenol.

This example teaches the use of an electrochemical detector in the invention. This example also teaches the determination of relatively low concentrations of two phenolic compounds.

What is claimed is:

1. Apparatus for membrane assisted liquid chromatography, comprising:
   a means for pumping a liquid;
   a membrane having a first side and a second side;
   a channel having a first end and a second end, at least a portion of the channel being formed by the first side of the membrane so that the second side of the membrane can be exposed to a sample containing a sample component;
   an injection conduit having a first end and a second end for containing a preselected volume of the the liquid;
   a liquid chromatography column for chromatographing the sample component, the liquid chromatography column having an inlet port;
   a means for switching liquid flow between a first flow pattern and a second flow pattern, the means for switching having distinct ports and being in liquid communication with the means for pumping the liquid, with the first end of the channel, with the second end of the channel, with the first end of the injection conduit, with the second end of the injection conduit, and with the inlet port of the chromatography column at said distinct ports, the first flow pattern being from the pumping through the channel and then through the injection conduit, the second flow pattern being from the same means for pumping as the first flow pattern, through the injection conduit, and then to the inlet port of the liquid chromatography column.

2. The apparatus of claim 1 wherein the membrane is tubular in shape.

3. The apparatus of claim 1 wherein the injection conduit is an injection loop.

4. The apparatus of claim 1 wherein the liquid chromatography column is of the packed type.

5. The apparatus of claim 1 wherein the liquid chromatography column is of the capillary type.

6. The apparatus of claim 1 wherein the means for switching liquid flow is a two position 10-port valve.

7. The apparatus of claim 1 wherein the means for switching liquid flow is a two position 8-port valve.

8. The apparatus of claim 1 wherein the means for switching liquid flow is a pair of two position 6-port valves.

* * * * *

UNITED STATES PATENT AND TRADEMARK OFFICE
CERTIFICATE OF CORRECTION

PATENT NO. : 4,999,105

DATED : Mar. 12, 1991

INVENTOR(S) : Richard G. Melcher; Hernan J. Cortes

It is certified that error appears in the above-identified patent and that said Letters Patent is hereby corrected as shown below:

Column 8:
Claim 1, line 35, after "from the" insert --means for--.

Signed and Sealed this

Tenth Day of November, 1992

Attest:

DOUGLAS B. COMER

Attesting Officer

Acting Commissioner of Patents and Trademarks